United States Patent
Tan et al.

(10) Patent No.: US 11,642,350 B2
(45) Date of Patent: May 9, 2023

(54) AGENT FOR PREVENTING MYOPIA, TREATING MYOPIA, AND/OR PREVENTING MYOPIA PROGRESSION COMPRISING TIOTROPIUM AS ACTIVE INGREDIENT

(71) Applicants: Singapore Health Services PTE LTD, Singapore (SG); Santen Pharmaceutical Co., Ltd., Osaka (JP)

(72) Inventors: Tiang Hwee Donald Tan, Singapore (SG); Roger Wilmer Beuerman, Singapore (SG); Seang-Mei Saw, Singapore (SG); Aradhana Upadhyay, Singapore (SG); Masatomo Kato, Ikoma (JP); Takaaki Inaba, Ikoma (JP)

(73) Assignees: Singapore Health Services PTE LTD, Singapore (SG); Santen Pharmaceutical Co., Ltd., Osaka (JP)

( * ) Notice: Subject to any disclaimer, the term of this patent is extended or adjusted under 35 U.S.C. 154(b) by 10 days.

(21) Appl. No.: 16/495,350

(22) PCT Filed: Mar. 22, 2018

(86) PCT No.: PCT/JP2018/011361
§ 371 (c)(1),
(2) Date: Sep. 18, 2019

(87) PCT Pub. No.: WO2018/174149
PCT Pub. Date: Sep. 27, 2018

(65) Prior Publication Data
US 2020/0147098 A1 May 14, 2020

(30) Foreign Application Priority Data
Mar. 23, 2017 (SG) .............. 10201702378S

(51) Int. Cl.
*A61K 31/5386* (2006.01)
*A61P 27/10* (2006.01)
*A61K 9/00* (2006.01)

(52) U.S. Cl.
CPC ........ *A61K 31/5386* (2013.01); *A61K 9/0048* (2013.01); *A61P 27/10* (2018.01)

(58) Field of Classification Search
CPC .... A61K 31/5386; A61K 9/0048; A61P 27/10
See application file for complete search history.

(56) References Cited

U.S. PATENT DOCUMENTS

| | | | |
|---|---|---|---|
| 2002/0110529 A1 | 8/2002 | Bechtold-Peters et al. | |
| 2002/0169321 A1* | 11/2002 | Banholzer ............ | C07D 451/10 546/91 |
| 2015/0366854 A1* | 12/2015 | Ostrow ................... | A61P 43/00 514/304 |
| 2016/0009705 A1* | 1/2016 | Ostrow ................... | A61K 9/08 514/304 |
| 2019/0151270 A1* | 5/2019 | Ashby .................... | A61K 45/06 |

FOREIGN PATENT DOCUMENTS

| | | |
|---|---|---|
| WO | WO 1996/013262 A1 | 5/1996 |
| WO | WO 2002/030389 A1 | 4/2002 |
| WO | WO 2009/045172 A1 | 4/2009 |
| WO | WO 2012/161655 A1 | 11/2012 |
| WO | WO 2016/205068 | 12/2016 |
| WO | WO 2016/205069 A1 | 12/2016 |

OTHER PUBLICATIONS

Barnes, "Tiotropium bromide", 2001, Expert Opinion on Investigational Drugs, 10(4), pp. 733-740. (Year: 2001).*
International Search Report and Written Opinion dated May 29, 2018 for International Application No. PCT/JP2018/011361; 8 pages.
Barathi et al., 2013, "Muscarinic cholinergic receptor (M2) plays a crucial role in the development of myopia in mice", Disease Models & Mechanisms, 6(5):1146-1158.
Barnes et al., 1995, "Tiotropium bromide (Ba 679 BR), a novel long-acting muscarinic antagonist for the treatment of obstructive airways disease", Life Sciences, 56(11/12):853-859.
Luft et al., 2003, "Variable effects of previously untested muscarinic receptor antagonists on experimental myopia", Investigative Ophthalmology & Visual Science, 44(3):1330-1338.
Mitchelson et al., 2012, "Muscarinic Receptor Agonists and Antagonists: Effects on Ocular Function", Handbook of Experimental Pharmacology 208:263-298.
Extended European Search Report dated Nov. 2, 2020 for European Pat. App. No. 18772076.8 (7 pages).
Lin et al., 2016, "Role of Chronic Inflammation in Myopia Progression: Clinical Evidence and Experimental Validation", EBioMedicine, vol. 10:269-281.
Barnes, P. J., 2001, "Tiotropium bromide," Expert Opinion on Investigational Drugs, 10(4):733-740 (8 pages).
Li et al., 2009, "Cough," China Pharmaceutical Technology Press, pp. 183-184 (with English Translation).
Zhang et al., 2008, "Clinical diagnosis and pharmaceutical administration of asthma," Fourth Military Medical University Press, pp. 107-108 (with English Translation).

* cited by examiner

*Primary Examiner* — Michael B. Pallay
(74) *Attorney, Agent, or Firm* — Jones Day

(57) ABSTRACT

The present invention relates to an agent for preventing myopia, treating myopia, and/or preventing myopia progression, comprising tiotropium as an active ingredient.

9 Claims, No Drawings

AGENT FOR PREVENTING MYOPIA, TREATING MYOPIA, AND/OR PREVENTING MYOPIA PROGRESSION COMPRISING TIOTROPIUM AS ACTIVE INGREDIENT

CROSS REFERENCE TO RELATED APPLICATIONS

This application is a national stage entry of International Patent Application No. PCT/JP2018/011361, filed Mar. 22, 2018, which claims the benefit of Singapore Patent Application No. 10201702378S, filed Mar. 23, 2017, the disclosure of each of which is incorporated by reference herein in its entirety.

TECHNICAL FIELD

The present invention mainly relates to an agent for preventing myopia, treating myopia, and/or preventing myopia progression, comprising tiotropium as an active ingredient.

BACKGROUND ART

Myopia is a form of ametropia, which is a pathology that the eyesight blurs because the light from a long distance which enters eyes makes an image before retina. In case that the refractive power of cornea/lens is too strong, when a person looks into the far distance, the image is not focused on retina, but focused before retina. Such myopia is referred to as refractive myopia. On the other hand, in case that the axial length which is the length between cornea and retina is extended, i.e., too longer than normal, when a person looks into the far distance, the image is not focused on retina, but focused before retina, even though the thickness of lens is reduced. Such myopia is referred to as axial myopia. The development of myopia at an early age or fast progression of myopia may lead to high myopia as an adult with associated visually disabling pathologic myopia lesions. In order to prevent myopia, treat myopia, and/or prevent myopia progression, various studies based on surgery, optical wear or medication have been tried.

Atropine is known as its sulfate hydrate form shown below, which has a preventing action on myopia progression by reducing axial elongation (Patent Literature 1). However, atropine has a significant dose-related mydriatic action, which may result in unacceptable glare and photophobia, a loss of depth of focus, and potentially allowing more UV light entry into the eye. Atropine also reduces normal accommodation in a dose dependent manner, which can result in poor near vision. These side-effects reduce the clinical effectiveness of using high concentrations of atropine in the clinical setting, although low dose atropine has been shown to still be effective in reducing axial elongation, but with less mydriasis and accommodation loss.

[Chem. 1]

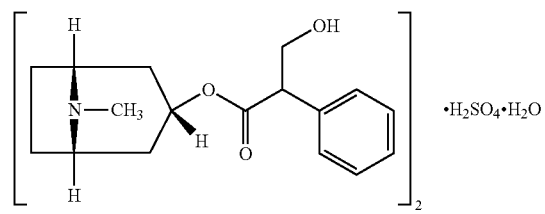

In the meantime, tiotropium, in particular, tiotropium bromide hydrate (hereinafter, "tiotropium bromide hydrate" may be also referred to as just "tiotropium"), is a compound represented by the following chemical formula, which has been on sale as an inhalant liquid formulation (Spiriva™) which can relieve various symptoms based on obstructive airway disorder in chronic obstructive pulmonary disease (COPD).

[Chem. 2]

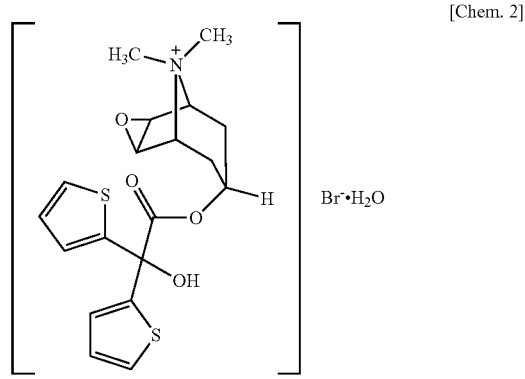

Patent Literature 2 discloses an inhalant formulation comprising tiotropium for treating COPD and asthma. However, there has not been reported about the effect of tiotropium through the ocular topical administration, in particular, about its effect preventing myopia, treating myopia, and/or preventing myopia progression.

CITATION LIST

Patent Literature

[Patent Literature 1] WO 2012/161655
[Patent Literature 2] WO 2002/030389

SUMMARY OF INVENTION

Technical Problem

The purpose of the present invention may be to find a novel compound useful for preventing myopia, treating myopia, and/or preventing myopia progression. In addition, the purpose of the present invention may be to find a novel compound useful for preventing myopia, treating myopia, and/or preventing myopia progression with reduced side-effects due to mydriatic action.

Solution to Problem

The present inventors have intensively studied to solve the aforementioned problem and have discovered that tiotropium which is used in the treatment of chronic obstructive pulmonary disease (COPD) can suppress the axial length elongation, and tiotropium is therefore useful for preventing myopia, treating myopia, and/or preventing myopia progression. In addition, the present inventors have also found that tiotropium has the effect suppressing the axial length elongation even in much lower dose than atropine, and further has a lower mydriatic action which is a side-effect than atropine. Based upon the new findings, the present invention has been completed.

The present invention may relates to the followings.

(Term 1) An agent for preventing myopia, treating myopia, and/or preventing myopia progression, comprising tiotropium or a salt thereof or a hydrate thereof as an active ingredient.

(Term 2) The agent of Term 1, characterized in that the agent does not substantially have mydriatic action.

(Term 3) The agent of Term 1 or 2, wherein the concentration of tiotropium or a salt thereof or a hydrate thereof is about 0.000001 to about 5% (w/v).

(Term 4) The agent of Term 1 or 2, wherein the concentration of tiotropium or a salt thereof or a hydrate thereof is about 0.00001 to about 2% (w/v).

(Term 5) The agent of Term 1 or 2, wherein the concentration of tiotropium or a salt thereof or a hydrate is about 0.0001 to about 2% (w/v).

(Term 6) The agent of Term 1 or 2, wherein the concentration of tiotropium or a salt thereof or a hydrate is about 0.0001 to about 1% (w/v).

(Term 7) The agent of Term 1 or 2, wherein the concentration of tiotropium or a salt thereof or a hydrate is about 0.0001 to about 0.1% (w/v).

(Term 8) The agent of Term 1 or 2, wherein the concentration of tiotropium or a salt thereof or a hydrate is about 0.0001 to about 0.01% (w/v).

(Term 9) The agent of any one of Terms 1 to 8, which is for ocular topical administration.

(Term 10) The agent of Term 9, wherein the ocular topical administration is instillation administration or intravitreal administration.

(Term 11) The agent of any one of Terms 1 to 10, whose formulation type is eyedrop, eye gel, ophthalmic ointment or injection.

(Term 12) The agent of any one of Terms 1 to 11, wherein tiotropium or a salt thereof or a hydrate thereof is tiotropium bromide hydrate.

(Term 13) An agent for suppressing the axial length elongation, comprising tiotropium or a salt thereof or a hydrate thereof as an active ingredient.

(Term 14) Use of tiotropium or a salt thereof or a hydrate thereof in the manufacture of an agent for preventing myopia, treating myopia, and/or preventing myopia progression.

(Term 15) Tiotropium or a salt thereof or a hydrate thereof for use in preventing myopia, treating myopia, and/or preventing myopia progression.

(Term 16) A pharmaceutical composition comprising tiotropium or a salt thereof or a hydrate thereof for use in preventing myopia, treating myopia, and/or preventing myopia progression.

(Term 17) A method for preventing myopia, treating myopia, and/or preventing myopia progression, comprising administering a therapeutically effective amount of tiotropium or a salt thereof or a hydrate thereof to a mammal in need thereof.

Effect of Invention

As shown in the experimental results mentioned below, it was demonstrated that tiotropium can suppress the axial length elongation more potently than atropine. Thus, tiotropium is thought to be useful as a more potent agent for preventing myopia, treating myopia, and/or preventing myopia progression than atropine. In addition, it was also demonstrated that tiotropium has the effect suppressing the axial length elongation even in much lower dose than atropine, and further has a lower mydriatic action which is a side-effect than atropine, and hence tiotropium is expected to become a practical agent for preventing myopia, treating myopia, and/or preventing myopia progression with reduced side-effects disturbing daily life due to mydriatic action and/or accommodative loss.

DESCRIPTION OF EMBODIMENTS

Some embodiments of the present invention are explained in detail below.

The "agent for preventing myopia, treating myopia, and/or preventing myopia progression" used herein comprises tiotropium or a salt thereof or a hydrate thereof as an active ingredient.

The "salt of tiotropium" used herein is not limited as long as it is a salt with a pharmaceutically acceptable anion. For example, the salt includes a salt with hydroxide ion; a salt with an inorganic acid anion such as nitrate, sulfate and phosphate; a salt with an organic acid anion such as acetate, fumarate, maleate, succinate, citrate, tartrate, adipate, gluconate, glucoheptonate, glucuronate, terephthalate, methanesulfonate, lactate, hippurate, 1,2-ethanedisulfonate, isethionate, lactobionate, oleinate, pamoate, polygalacturonate, stearate, tannate, trifluoromethanesulfonate, benzenesulfonate, p-toluenesulfonate, laurylsulfate, methyl sulfate, naphthalenesulfonate, and sulfosalicylate; and a salt with a halogen ion such as bromine ion, fluorine ion, chlorine ion, and iodine ion. In the present invention, the particularly preferred salt of tiotropium is the salt with bromine ion.

The chemical name of "tiotropium bromide" is (1α,2β,4β,5α,7β)-7-[(hydroxydi-2-thienylacetyl)oxy]-9,9-dimethyl-3-oxa-9-azoniatricyclo[3.3.1.0$^{2,4}$]nonane bromide, whose chemical structure is shown below.

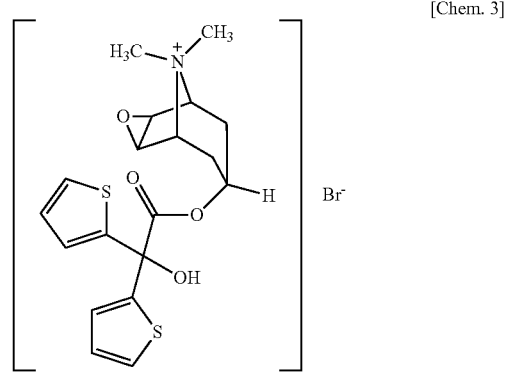

[Chem. 3]

And, the "tiotropium or a salt thereof" may be in a hydrate form or in a solvate form. Preferred hydrate thereof is monohydrate.

The chemical name of "tiotropium bromide hydrate" is (1α,2β,4β,5α,7β)-7-[(hydroxydi-2-thienylacetyl)oxy]-9,9-dimethyl-3-oxa-9-azoniatricyclo[3.3.1.0$^{2,4}$]nonane bromide monohydrate, whose chemical structure is shown below.

[Chem. 4]

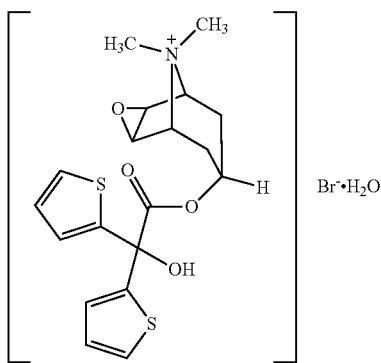

When "tiotropium or a salt thereof or a hydrate thereof" is a geometric isomer or an optical isomer, the present invention encompasses these isomers. And, when "tiotropium or a salt thereof or a hydrate thereof" has a proton tautomer, the present invention also encompasses such tautomer or a salt thereof.

When "tiotropium or a salt thereof or a hydrate thereof" has a polymorphism and a polymorphism group (polymorphism system), the present invention also encompasses these polymorphism and polymorphism group (polymorphism system). The polymorphism group (polymorphism system) used herein means a crystal form at the respective stages and the entire course when the crystal form is changed with the conditions and states of preparation, crystallization, preservation, etc.

The "tiotropium or a salt thereof or a hydrate thereof" can be prepared in a general manner or can be also obtained as a commercially available product. For example, tiotropium bromide hydrate is commercially offered by AvaChem Corp (product code: 2984H).

The concentration of "tiotropium or a salt thereof or a hydrate thereof" used herein is not particularly limited, but it may be, for example 0.000001 to 5% (w/v), and 0.00001-2% (w/v), preferably 0.0001 to 2% (w/v), and 0.0001-1% (w/v), more preferably 0.0001-0.1% (w/v), even more preferably 0.0001-0.01% (w/v), in case of eyedrops.

The concentration of "tiotropium or a salt thereof or a hydrate thereof" used herein may mean a concentration of free form of tiotropium, or a concentration of a salt thereof or a salt hydrate thereof.

The term "not substantially have mydriatic action" in the present invention means that the agent has no mydriatic action of the level to disturb daily life. Hence, even if mydriatic action is found in any measuring way, it is interpreted as "not substantially have mydriatic action" when the treated patient does not experience visual side-effects of glare and pupil dilation which disturbs his/her daily life.

The "myopia" in the present invention is defined as a refractive state of an uncorrected eye where light rays meet the eye before the retina. The "myopia" in the present invention includes all and every known classification and definition of myopia including axial myopia, refractive myopia, pathological myopia, simple myopia, extreme myopia, severe myopia, strong myopia, moderate myopia, and light myopia.

The "agent for preventing myopia, treating myopia, and/or preventing myopia progression" used herein includes an agent for preventing refractive myopia, treating refractive myopia, and/or preventing refractive myopia progression and an agent for preventing axial myopia, treating axial myopia, and/or preventing axial myopia progression, preferably an agent for preventing axial myopia, treating axial myopia, and/or preventing axial myopia progression. The term "preventing myopia progression" used herein may mean slowing myopia progression or reducing myopia progression. The term "preventing myopia" used herein may mean preventing the onset of myopia or delaying the onset of myopia.

As shown in the experimental results mentioned below, tiotropium can suppress the axial length elongation, and hence the present invention may also include an agent for suppressing the axial length elongation, comprising tiotropium or a salt thereof or a hydrate thereof as an active ingredient.

The "tiotropium or a salt thereof or a hydrate thereof" in the present invention is preferably used for preventing myopia, treating myopia and/or preventing myopia progression, in particular more preferably, for preventing myopia in schoolage children or in teenagers or adults with myopia progression and/or for preventing myopia progression in schoolage children or in teenagers or adults with myopia progression.

The usage of the "agent for preventing myopia, treating myopia, and/or preventing myopia progression" in the present invention can vary depending on dosage form; symptom severity; age, age of onset of myopia, parental myopia, body weight of patient in need thereof; physician's discretion; etc. As for eyedrops, the agent can be administered in eyedrops, for example, every day to every one week, preferably every day, in an amount of 1-5 drops each time, preferably 1-3 drops each time, more preferably 1-2 drops each time, even more preferably 1 drop each time, at a frequency of 1-4 times a day, preferably 1-3 times a day, more preferably once or twice a day, particularly preferably once a day. Preferably, it is administered in eyedrops every day, with 1 drop once a day.

In the present invention, tiotropium can be administered topically, orally, or parenterally, and the administration style thereof includes an ocular topical administration including sustained continuous delivery to the eye (instillation administration, administration of an ophthalmic ointment, conjunctival sac administration, intravitreal administration, subconjunctival administration, Tenon capsule administration, etc.), an oral administration, an intravenous administration, and a transdermal administration.

Preferred formulations for topically-administering tiotropium to eyes include an eyedrop, an eye gel and an ophthalmic ointment, and also an injection thereof can be used for this administration, particularly an injection for subconjunctival administration, Tenon capsule administration or intravitreal administration. The present formulation comprising tiotropium as an active ingredient can be prepared with optionally-necessary pharmaceutically-acceptable additives by forming it to a dosage form suitable for a desired administration.

In the present invention, a dosage form suitable for oral administration includes, for example, a tablet, a capsule, a granule, and a powder, and a dosage form suitable for parenteral administration includes, for example, an injection, an eyedrop, an eye gel, an ophthalmic ointment, a patch, a gel, and an intercalating agent. These dosage forms can be prepared in a general manner used widely in the art.

In order to sustain the therapeutic effect of the present invention further effectively, a DDS formulation such as a formulation for intraocular implant and a microsphere can be used.

The eyedrop can be prepared with some optional additives selected from, for example, a tonicity agent, a buffer agent, a surfactant, a stabilizing agent, a preservative, or the like, as needed. The pH of the eyedrop is not limited as long as the pH is in an acceptable range for ophthalmic formulations, generally a range of 2-8 is preferable. The tonicity agent includes, for example, sodium chloride. The buffer agent includes, for example, sodium phosphate and sodium acetate. The surfactant includes, for example, polyoxyethylene sorbitan monooleate, polyoxyl 40 stearate, and polyoxyethylene hydrogenated castor oil. The stabilizing agent includes, for example, sodium citrate, and disodium edetate. The preservative includes, for example, benzalkonium chloride and paraben.

When the formulation of the present invention comprising tiotropium as an active ingredient is an eyedrop, an eye gel or an ophthalmic ointment, the formulation may comprise a preservative agent or may not.

The ophthalmic ointment can be prepared with a widely-used base material such as white petrolatum and liquid paraffin.

The tablet can be prepared with some optional additives selected from, for example, an excipient, a disintegrant, a binder, a lubricant, a coating agent, a flavor, or the like, as needed. The excipient includes, for example, lactose, glucose, D-mannitol, anhydrous dibasic calcium phosphate, starch, and sucrose. The disintegrant includes, for example, carboxymethylcellulose, carboxymethylcellulose calcium, croscarmellose sodium, crospovidone, starch, partially-pregelatinized starch, and low substituted hydroxypropylcellulose. The binder includes, for example, hydroxypropylcellulose, ethylcellulose, gum arabic, starch, partially-pregelatinized starch, polyvinylpyrrolidone, and polyvinyl alcohol. The lubricant includes, for example, magnesium stearate, calcium stearate, talc, hydrated silicon dioxide, and hydrogenated oil. The coating agent includes, for example, purified sucrose, hydroxypropylmethylcellulose, hydroxypropylcellulose, methylcellulose, ethylcellulose, and polyvinylpyrrolidone. The flavor includes, for example, citric acid, aspartame, ascorbic acid, and menthol.

The injection can be prepared with some optional additives selected from, for example, a tonicity agent, a buffer agent, a surfactant, a thickener, or the like, as needed. The tonicity agent includes, for example, sodium chloride. The buffer agent includes, for example, sodium phosphate. The surfactant includes, for example, polyoxyethylene sorbitan monooleate. The thickener includes, for example, methylcellulose.

For example, the intercalating agent can be prepared by mixing and milling tiotropium and a biodegradable polymer such as hydroxypropylcellulose, hydroxypropylmethylcellulose, carboxy vinyl polymer, and polyacrylic acid, and then compacting the obtained powder. As appropriate, an excipient, a binder, a stabilizing agent, and/or a pH adjuster may be used therein.

For example, the formulation for intraocular implant can be prepared with a biodegradable polymer such as polylactide, polyglycolate, lactide-glycolate copolymer, and hydroxypropylcellulose.

When tiotropium is topically administered to the eyes in the form of an eyedrop, it is preferred that the eyedrop contains tiotropium at such a concentration that the mydriatic action is not substantially caused when topically administered to the rabbit's eyes or mouse's eyes. The concentration is, for example, less than about 5% (w/v), less than about 4% (w/v), less than about 3% (w/v), less than about 2% (w/v), less than about 1.5% (w/v), less than about 1% (w/v), less than about 0.5% (w/v), less than about 0.2% (w/v), less than about 0.1% (w/v), less than about 0.05% (w/v), less than about 0.01% (w/v), less than about 0.001% (w/v) or less than about 0.0001% (w/v).

When tiotropium is topically administered to the eyes in the form of an eyedrop, it is preferred that the eyedrop contains tiotropium at such a concentration that the axial length elongation is substantially suppressed when topically administered to the mouse's eyes. The concentration is, for example, not less than about 0.000001% (w/v), not less than about 0.00001% (w/v), not less than about 0.0001% (w/v), not less than about 0.001% (w/v), not less than about 0.01% (w/v), not less than about 0.1% (w/v), not less than about 0.2% (w/v), not less than about 0.5% (w/v), or not less than about 1% (w/v). In more detail, the concentration of tiotropium should not be limited as long as the range thereof is in 0.000001-about 5% (w/v), which includes, for example, preferably about 0.00001-about 2% (w/v), about 0.00001-about 1% (w/v), about 0.00001-about 0.1% (w/v), about 0.00001-about 0.01% (w/v), about 0.0001-about 2% (w/v), about 0.0001-about 1% (w/v), about 0.0001-about 0.1% (w/v), about 0.0001-about 0.01% (w/v), about 0.001-about 2% (w/v), about 0.001-about 1% (w/v), about 0.001-about 0.1% (w/v), about 0.001-about 0.01% (w/v), about 0.01-about 2% (w/v), about 0.01-about 1% (w/v), or about 0.01-about 0.1% (w/v); more preferably about 0.00001-about 2% (w/v); much more preferably about 0.0001-about 2% (w/v); the most preferably about 0.0001-about 1% (w/v); even more preferably about 0.0001-about 0.1% (w/v); and particularly about 0.0001-about 0.01% (w/v). The "about" mentioned above means error range of 5%.

EXAMPLES

Here is each test result and formulation examples, which are shown in order to make it easy to understand the present invention, but should not be limited thereto.

Test 1. Test About Suppression of Axial Length Elongation in Myopia Chick Model (Preparation of Test Sample)

Tiotropium bromide hydrate was dissolved in saline to prepare 0.1 mM and 10 mM tiotropium solutions.

And, atropine sulfate hydrate was dissolved in saline to prepare 100 mM atropine solution as a reference example.

As a control, saline was used.

(Test Method and Administration Method)

A test tube having a diameter of 18 mm was cut off at the level of 10 mm from the bottom, and the cutting circle of the cut-off bottom part was bonded to a flat rubber packing with an adhesive agent to prepare a lens (goggle). 7-day-old chicks (white leghorns) were obtained, and the prepared goggle was attached to the right eye of each chick with an adhesive agent to induce myopia to the chicks. The left eye thereof was its control.

To each of the tiotropium administration groups, 20 µL of each prepared tiotropium solution was intravitreally administered on the day that the goggle was fixed (on day 0), on day 2, and on day 4. In the same way as the procedure in the tiotropium administration groups, 20 µL of the atropine solution was intravitreally administered to the atropine administration group, and 20 µL of saline was intravitreally administered to the control group. In the all groups, 20 µL of saline was intravitreally administered to the left eye of each chick, on day 0, day 2, and day 4.

The chicks were reared under a normal rearing condition.

(Evaluation)

On day 6 from the myopia induction, the axial length of right and left eyeballs was measured with a ultrasound axial length measurement ECHOSCAN US-500 (NIDEK CO., LTD.) (A-scan). The difference of axial lengths and the suppression rate of the axial length elongation were calculated by the following formulae.

Difference of axial lengths (mm) =

[axial length (mm) of right eye] − [axial length (mm) of left eye]

Suppression rate of axial length elongation (%) =

$$\left(1 - \frac{[\text{Difference of axial lengths in drug administration group}]}{[\text{Difference of axial lengths in control group}]}\right) \times 100$$

(Test Result)

The suppression rates of the axial length elongation in the tiotropium administration group and the atropine administration group are shown in Table 1. The ">100" in Table 1 denotes that the suppression rate is over 100%.

TABLE 1

| Drug administration group | | Suppression rate (%) |
|---|---|---|
| 0.1 mM | tiotropium | 45 |
| 10 mM | tiotropium | >100 |
| 100 mM | atropine | 83 |

The suppression rate in 100 mM atropine administration group including the high concentration drug was 83%. Whereas, the suppression rate in 0.1 mM tiotropium administration group was 45%, though the concentration thereof is one thousandth of the atropine's concentration. And, the suppression rate in 10 mM tiotropium administration group was over 100%, though the concentration thereof is one tenth of the atropine's concentration.

(Discussion)

As clearly exhibited in Table 1, it has been found that tiotropium can suppress the axial length elongation more potently than atropine. Thus, it is thought that tiotropium is useful as a more potent agent for preventing myopia, treating myopia, and/or preventing myopia progression than atropine.

Test 2. Test About Suppression of Axial Length Elongation in Myopia Mice Model (Preparation of Test Sample)

Tiotropium bromide hydrate and glycerin were dissolved in water for injection to prepare 0.0001% (w/v) and 0.01% (w/v) tiotropium ophthalmic solutions without adjusting pH. In a similar way, atropine sulfate hydrate and glycerin were dissolved in water for injection to prepare 0.1% (w/v) atropine ophthalmic solution without adjusting pH. The vehicle (control) was isotonic water which was prepared with water for injection and glycerin.

(Test Method)

Murine Model of Experimental Myopia:

Spectacle lens-induced myopia model was established by placing −15D hard lens on the right eye of mice (C57BL/6J), which was served as the experimental eye, at post-natal days 18. Briefly, a −15D lens was glued to an annulus (with 8 mm base curve) of Velcro. This mating piece was then attached to the Velcro that had been previously glued to the hair around the right experimental eye using a cyanoacrylate. An air gap of 1.5 mm existed between the back part of the lens and the anterior surface of the cornea.

Ocular Biometry Methods:

Ocular biometry such as axial length measurement was done using in vivo Optical Low Coherence Interferometry (OLCI-AcMaster). The axial length was measured at post-natal days 33 and 61.

The ratio for suppressing the axial length elongation with each example was calculated by the following equation:

Mean values for the changes in the axial length ($\mu$m) = [axial length on day 61] − [axial length on day 33]

Supression rate (%) of axial length elongation =

$$\left(1 - \frac{\left[\begin{array}{c}\text{Change in axial lengths in drug}\\ \text{administration group or no lens group}\end{array}\right]}{[\text{Change in axial lengths in vehicle administration group}]}\right) \times 100$$

(Drug Treatment)

Tiotropium (at 0.0001% or 0.01%) or atropine (at 0.1%) was administered once a day post-natal day 33 until day 61 in the spectacle lens-induced myopia model. 7 μL of each drug was administered topically to the right eye in dim red light at the each day.

| Groups | N | Lens | |
|---|---|---|---|
| Lens with vehicle | 7 | R | + |
| | | L | − |
| Lens with 0.0001% tiotropium | 7 | R | + |
| | | L | − |
| Lens with 0.01% tiotropium | 7 | R | + |
| | | L | − |
| Lens with 0.1% atropine | 7 | R | + |
| | | L | − |
| No lens (naive) | 7 | R | − |
| | | L | − |

(Test Result)

The mean values and suppression rates of the axial length elongation in the tiotropium administration group and the atropine administration group are shown in Table 2.

TABLE 2

Mean values for the changes in the axial length and the calculated suppression rates

| | Mean (μm) | Suppression rate (%) |
|---|---|---|
| Vehicle | 158.31 | 0 |
| 0.0001% Tiotropium | 135.84 | 14.20 |
| 0.01% Tiotropium | 112.95 | 28.66 |
| 0.1% Atropine | 111.61 | 29.50 |
| No lens (naive) | 136.44 | 13.82 |

(Discussion)

The suppression rate of axial length elongation in 0.1% atropine group was 29.50%. On the other hand, 0.01% tiotropium group which was one tenth of the concentration in the atropine group exhibited the same level of suppression rate as 0.1% atropine group. Further, 0.0001% tiotropium group exhibited the same level of suppression rate as the normal group (no lens), which indicates it can sufficiently suppress the axial length elongation.

As above mentioned, it has been found that tiotropium can suppress the axial length elongation more potently than atropine, even by eyedrop administration. Furthermore, it has been found that tiotropium can suppress the axial length elongation even in low concentration.

Test 3. Evaluation of Mydriatic Action (Preparation of Test Sample)

Tiotropium bromide hydrate and glycerin were dissolved in water for injection to prepare 0.01% (w/v), 0.1% (w/v), and 2% (w/v) tiotropium ophthalmic solutions without adjusting pH.

In a similar way, atropine sulfate hydrate and glycerin were dissolved in water for injection to prepare 0.01% (w/v), and 0.1% (w/v) atropine ophthalmic solutions without adjusting pH.

(Test Method)

A single dose (5 µL) of each prepared ophthalmic solution was administered to both eyes of mice (6 eyes of 3 mice per each ophthalmic solution). Before the administration (eyedrop), and 1, 2, 4 and 24 hours after the administration, each pupil diameter of the mice was measured. The measured pupil diameters of the mice at each measurement time per each test sample were averaged to obtain each average value as each average pupil diameter. Among each average pupil diameter at each measurement time, the longest diameter was defined as the maximum pupil diameter.

(Test Result)

The results are shown in Table 3.

TABLE 3

| | Pupil diameter before administration (mm) | Maximum pupil diameter (mm) | Measurement time of maximum pupil diameter (h) |
|---|---|---|---|
| Control | 0.36 | 0.37 | 24 |
| 0.01% Tiotropium | 0.36 | 1.24 | 4 |
| 0.1% Tiotropium | 0.43 | 2.23 | 2 |
| 2% Tiotropium | 0.36 | 2.15 | 1 |
| 0.01% Atropine | 0.42 | 1.43 | 1 |
| 0.1% Atropine | 0.40 | 1.96 | 2 |

(Discussion)

Table 3 showed that the maximum pupil diameter of 0.01% tiotropium ophthalmic solution group was smaller than that of 0.01% atropine ophthalmic solution group. In addition, Tests 1 and 2 showed that the effect suppressing the axial length elongation with tiotropium is more potent than that of atropine, and even a low concentration of tiotropium exhibits the suppression effect. Thus, tiotropium is useful as an agent for preventing myopia progression or treating myopia, whose side-effect of mydriatic action is reduced.

Formulation Example

The agents of the present invention are explained in detail by referring formulation examples, but should not be limited only thereto.

Formulation Example 1: Eyedrop (0.01% (w/v))

| in 100 ml | |
|---|---|
| tiotropium bromide hydrate | 0.01 g |
| sodium chloride | 0.9 g |

| | |
|---|---|
| disodium hydrogen phosphate | q.s. |
| sodium dihydrogen phosphate | q.s. |
| pH adjuster | q.s. |
| sterile purified water | q.s. |

The above eyedrop can be prepared by adding tiotropium bromide hydrate and the other ingredients shown in the above table to sterile purified water and then sufficiently mixing it. And, by changing the additive amount of tiotropium bromide hydrate, it is possible to prepare eyedrops having various concentrations, for example, an eyedrop having a concentration of 0.00001-2% (w/v).

Formulation Example 2: Injection

| in 10 ml | |
|---|---|
| tiotropium bromide hydrate | 10 mg |
| sodium chloride | 90 mg |
| polysorbate 80 | q.s. |
| sterile purified water | q.s. |

The above injection can be prepared by adding tiotropium bromide hydrate and the other ingredients shown in the above table to sterile purified water and then sufficiently mixing it to dissolve or suspend each ingredient. And, by suitably changing the additive amounts of tiotropium bromide hydrate and the other ingredients shown in the above table, it is possible to prepare injections having various concentrations, for example, an injection having 0.01 mg-200 mg of tiotropium bromide hydrate in 10 ml thereof. The injection prepared in this way can be administered as an injection for intraocular administration such as an injection for intravitreal administration.

INDUSTRIAL APPLICABILITY

Tiotropium can suppress the axial length elongation, and tiotropium is useful for preventing myopia, treating myopia, and/or preventing myopia progression. And, tiotropium is expected as an agent for preventing myopia, treating myopia, and/or preventing myopia progression, which is characterized in that the agent does not substantially have mydriatic action and/or reduce accommodation.

The invention claimed is:

1. A method for treating or preventing myopia, comprising administering to a subject in need thereof a pharmaceutical composition comprising a therapeutically effective amount of tiotropium or a pharmaceutically acceptable salt and/or hydrate thereof as a sole active ingredient, and sterile purified water as a sole solvent, wherein the concentration of tiotropium or the salt and/or hydrate thereof in the pharmaceutical composition is from about 0.0001% to about 0.01% (w/v), the pharmaceutical composition is formulated as an eyedrop, and the administration does not cause substantial mydriatic action.

2. The method of claim 1, wherein the administration is an ocular topical administration.

3. The method of claim 2, wherein the ocular topical administration is instillation administration.

4. The method of claim 1, wherein the tiotropium or a pharmaceutically acceptable salt and/or hydrate thereof is tiotropium bromide hydrate.

5. A method for preventing myopia progression, comprising administering to a subject in need thereof a pharmaceutical composition comprising a therapeutically effective amount of tiotropium or a pharmaceutically acceptable salt and/or hydrate thereof as a sole active ingredient, and sterile purified water as a sole solvent, wherein the concentration of tiotropium or the salt and/or hydrate thereof in the pharmaceutical composition is from about 0.0001% to about 0.01% (w/v), the pharmaceutical composition is formulated as an eye-drop, and the administration does not cause substantial mydriatic action.

6. The method of claim 5, wherein the administration is an ocular topical administration.

7. The method of claim 6, wherein the ocular topical administration is instillation administration.

8. The method of claim 5, wherein the tiotropium or a pharmaceutically acceptable salt and/or hydrate thereof is tiotropium bromide hydrate.

9. A method for suppressing axial length elongation in a subject, comprising administering to the subject a pharmaceutical composition comprising a therapeutically effective amount of tiotropium or a pharmaceutically acceptable salt and/or hydrate thereof as a sole active ingredient, and sterile purified water as a sole solvent, wherein the concentration of tiotropium or the salt and/or hydrate thereof in the pharmaceutical composition is from about 0.0001% to about 0.01% (w/v), the pharmaceutical composition is formulated as an eye-drop, and the administration does not cause substantial mydriatic action.

* * * * *